United States Patent [19]

Haury

[11] 3,950,421

[45] Apr. 13, 1976

[54] METHOD OF PRODUCING TRIAMINOGUANIDINE NITRATE

[75] Inventor: Vernon E. Haury, Simi Valley, Calif.

[73] Assignee: Rockwell International Corporation, El Segundo, Calif.

[22] Filed: Sept. 13, 1974

[21] Appl. No.: 505,705

Related U.S. Application Data

[63] Continuation-in-part of Ser. No. 347,110, April 2, 1973, abandoned.

[52] U.S. Cl. ............................................. 260/564 F
[51] Int. Cl.² ........................................ C07C 133/10
[58] Field of Search .............................. 260/564 F

[56] References Cited

OTHER PUBLICATIONS

O'Connor et al., J. Applied Chemistry, Vol. 1, pp. 91–92, (1951).

*Primary Examiner*—Gerald A. Schwartz
*Attorney, Agent, or Firm*—L. Lee Humphries; Robert M. Sperry

[57] ABSTRACT

A method of producing triaminoguanidine nitrate wherein a source of free nitrate ions is provided in an aqueous medium during reaction of guanidine nitrate and hydrazine to increase the yield of triaminoguanidine nitrate.

5 Claims, No Drawings

METHOD OF PRODUCING TRIAMINOGUANIDINE NITRATE

CROSS-REFERENCE TO RELATED APPLICATIONS

This application is a continuation-in-part of U.S. Pat. application Ser. No. 347,110, filed April 2, 1973, now abandoned.

BACKGROUND OF THE INVENTION

1. Field of the Invention

This invention relates to chemical processing and is particularly directed to techniques for increasing the yield of triaminoguanidine nitrate from the aqueous reaction of guanidine nitrate and hydrazine.

2. Prior Art

Triaminoguanidine nitrate (TAGN) has been found to be extremely useful in formulating energetic compositions of matter, for use as gun propellants, and the like. Unfortunately, the prior art methods of producing TAGN have not been satisfactory. Conventionally, TAGN has been produced by reacting guanidine nitrate with hydrazine in an alcohol medium. However, this technique is relatively dangerous to perform and requires the use of high purity hydrazine, which is relatively expensive. Although this reaction typically provides yields of about 80%, product quality is poor. To overcome these disadvantages, the reaction has also been performed in an aqueous medium, rather than an alcohol medium. The use of the aqueous medium makes the reaction safer to perform and permits the use of dilute hydrazine, which affords a considerable reduction in cost. Unfortunately, prior art use of the aqueous medium for this reaction has provided yields of only about 30% to 60%. Thus, none of the prior art techniques for producing TAGN has been entirely satisfactory.

BRIEF SUMMARY AND OBJECTS OF THE INVENTION

These disadvantages of the prior art are overcome with the present invention and a method of producing TAGN is provided which obtains the advantages of using an aqueous medium for the reaction, while providing yields equal to those achieved with the alcohol medium and significantly reducing the time required for the reaction.

The advantages of the present invention are preferably attained by providing a source of free nitrate ions in the aqueous medium during the production of TAGN. In the preparation of TAGN the source of free nitrate ions may be accomplished by the direct addition of nitrate salts, such as ammonium nitrate or hydrazine nitrate, to the aqueous medium, or by adding nitric acid which reacts with the quanidine nitrate and hydrazine to provide such salts. It is found that the free nitrate ions serve to stabilize the triaminoguanidine in the hot aqueous solution. This stabilization avoids the necessity for recrystalization and provides increased yields and greater purity in the resulting products.

Accordingly, it is an object of the present invention to provide an improved method of producing TAGN.

Another object of the present invention is to provide a technique for improving the yield and reaction time of aqueous medium production of TAGN.

A specific object of the present invention is to provide a method of producing TAGN comprising providing a source of free nitrate ions in the aqueous medium during production of TAGN to increase the yield, while significantly reducing the reaction time.

These and other objects and features of the present invention will be apparent from the following detailed description.

DETAILED DESCRIPTION OF THE INVENTION

In that form of the present invention chosen for the purposes of illustration, TAGN is produced by reacting quanidine nitrate and hydrazine in an aqueous medium, while providing a source of free nitrate ions within the aqueous medium to increase the yield of TAGN, while significantly reducing the reaction time.

EXAMPLE I

A solution of 74.5 parts by weight of quanidine nitrate in 400 parts by weight of 37.5% aqueous hydrazine, with 12 parts by weight of ammonium nitrate added, was heated for one hour at 82°C to 102°C to expel the ammonia formed by the reaction. The triaminoguanidine nitrate crystalized in 68% yield on cooling to 10°C.

EXAMPLE II

Repeating Example I with 24 parts by weight of ammonium nitrate increased the yield of triaminoguanidine nitrate to 75%.

EXAMPLE III

Repeating Example I again, but with 48 parts by weight of ammonium nitrate, increased the yield to 83%.

EXAMPLE IV

A solution of 73.5 parts by weight of quanidine nitrate in a mixture of 230 parts by weight of 65% hydrazine, 125 parts by weight of water, and 55 parts by weight of 70% nitric acid was heated for one hour at 80°C to 103°C. Triaminoguanidine nitrate crystallized in 80% yield on cooling to 10°C.

EXAMPLE V

A solution of 73.5 parts by weight of quanidine nitrate in 215 parts by weight of 70% aqueous hydrazine in 180 parts by weight of water with 48 parts by weight of hydrazine nitrate added, was heated for one hour at 80°C to 104°C. Thereafter, upon cooling to 10°C, TAGN crystallized in 80% yield.

Obviously, numerous other variations and modifications may be made without departing from the present invention. Accordingly, it should be clearly understood that the forms of the present invention described above are illustrative only and are not intended to limit the scope of the present invention.

What is claimed is:

1. A method of producing triaminoguanidine nitrate, said method comprising the steps of:
    forming a source of free nitrate ions within an aqueous medium, and
    reacting guanidine nitrate with hydrazine in said aqueous medium to produce triaminoguanidine nitrate.

2. The method of claim 1 wherein said reacting step comprises:
    heating said aqueous medium and said reactants to a temperature in the range of about 80°C to 104°C for a period of about one hour, and subsequently cooling said aqueous medium and said reactants to about 10°C.

3. The method of claim 1 wherein said forming step consists of adding up to about 50 parts by weight of ammonium nitrate to about 250 parts by weight of said aqueous medium.

4. The method of claim 1 wherein said forming step consists of adding up to about 55 parts by weight of 70% nitric acid to about 250 parts by weight of said aqueous medium.

5. The method of claim 1 wherein said forming step consists of adding up to about 50 parts by weight of hydrazine nitrate to about 250 parts by weight of said aqueous medium.

* * * * *